United States Patent [19]

Baldwin

[11] Patent Number: 5,256,871
[45] Date of Patent: Oct. 26, 1993

[54] MACHINE FOR VIDEO INSPECTION OF GLASS CONTAINERS WITH INTERSECTING LIGHT BEAMS

[75] Inventor: Leo B. Baldwin, Horseheads, N.Y.

[73] Assignee: Emhart Glass Machinery Investments Inc., Wilmington, Del.

[21] Appl. No.: 994,658

[22] Filed: Dec. 22, 1992

[51] Int. Cl.⁵ .................... G01N 21/32; B07C 5/342
[52] U.S. Cl. .................... 250/223 B; 356/240
[58] Field of Search .................... 250/223 B; 356/240; 209/524, 526

[56] References Cited
U.S. PATENT DOCUMENTS

| | | | |
|---|---|---|---|
| 4,025,201 | 5/1977 | Deane | 250/223 B |
| 4,280,624 | 7/1981 | Ford | 250/223 B |
| 4,367,405 | 1/1983 | Ford | 250/223 B |
| 4,509,081 | 4/1985 | Peyton et al. | 250/223 B |
| 4,625,107 | 11/1986 | Planke | 250/223 B |
| 4,636,635 | 1/1987 | Kronseder | 250/223 B |

Primary Examiner—David C. Nelms
Assistant Examiner—Michael Messinger
Attorney, Agent, or Firm—Spencer T. Smith

[57] ABSTRACT

An inspection machine for inspecting the profile of a vertically standing glass bottle comprising a conveyor for horizontally displacing a vertically standing glass container through an inspection location, a pair of diffused light sources located behind the conveyor for directing beams of light horizontally at a container located at the inspection location, the beams being sufficiently large so that the light beams will pass around the entire profile of a container located at the inspection station, a mirror pair located in front of the conveyor for receiving each of the light beams and redirecting the beam rearwardly, a reflecting prism having a pair of angularly related reflecting surfaces, a two-dimensional camera having an imaging surface, a pair of mirrors for receiving the beams redirected from each of the mirror pairs and redirecting the received beams to reflect off a corresponding one of the prism reflecting surfaces onto a corresponding half of the imaging surface, means for evaluating the profile of both container images on the imaging surface, each of the mirrors receiving the light beam at an angle of no more than about 45°.

3 Claims, 2 Drawing Sheets

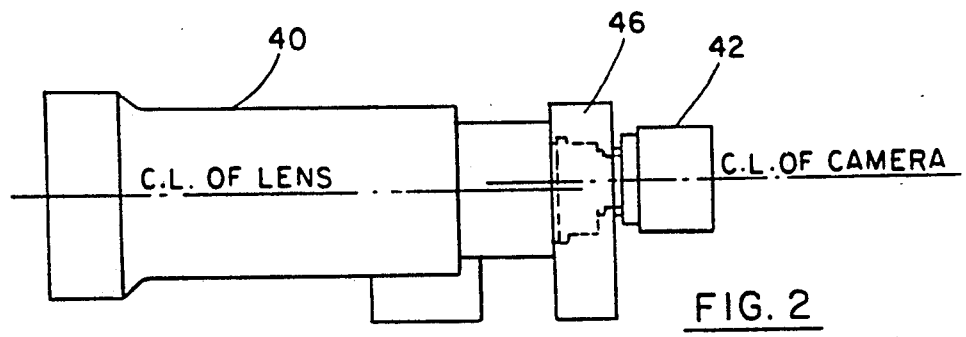
FIG. 2
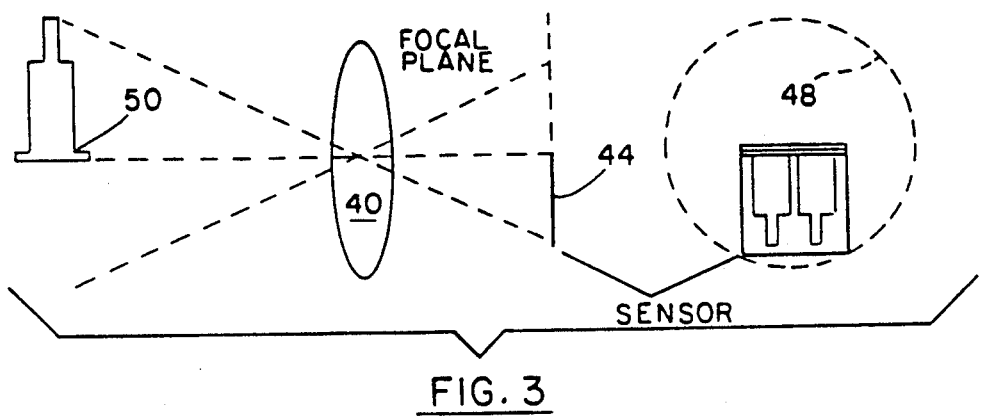
FIG. 3
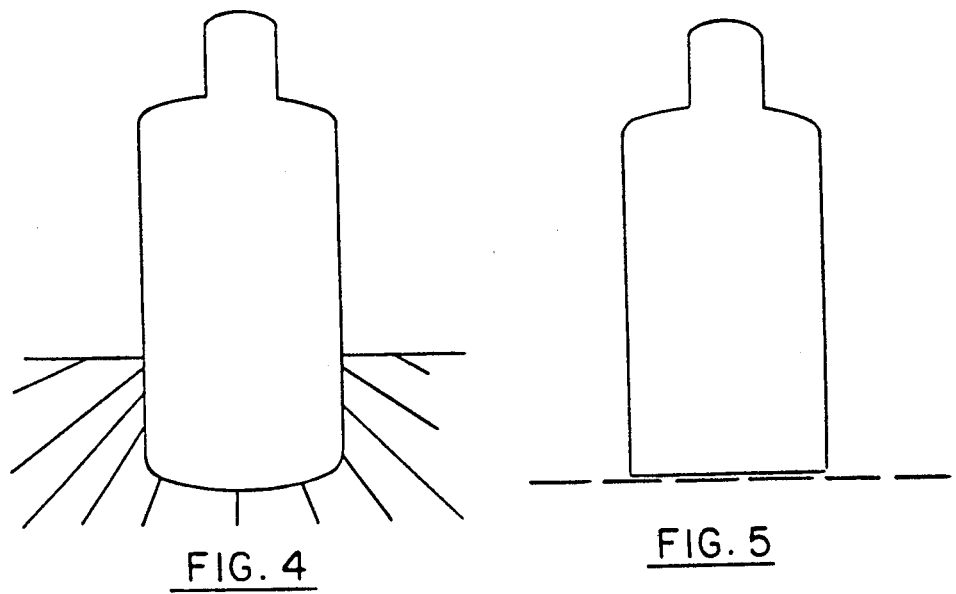
FIG. 4
FIG. 5

MACHINE FOR VIDEO INSPECTION OF GLASS CONTAINERS WITH INTERSECTING LIGHT BEAMS

FIELD OF THE INVENTION

The present invention relates to the sidewall inspection of glass containers.

Glass containers are made in glass forming machines from discrete gobs of molten glass. Many things can happen during this formation process which can adversely effect the formed container. Using a soda bottle as an example the formed bottle may improperly tilt or lean from its vertical axis. The bottle may have been unevenly heated resulting in the top half settling down relative to the bottom half causing the formation of a settle line which is unacceptable.

DESCRIPTION OF RELATED ART

To identify containers having these or other profile defects (cocked finish, bent, base leaner, diameter variation, freak), the entire profile of the container is inspected. Conventionally, the container, carried on a conveyor, passes through an inspection location where angularly related light sources direct light past the container profile to a pair of two-dimensional cameras which are located at some distance so that the entire profile can be imaged. Each camera image is evaluated by an image processor. Such systems are very expensive and require a large machine footprint. The requirement of dual cameras could be avoided by using a reflecting prism as shown in U.S. Pat. No. 4,025,201 but image quality would suffer.

It is accordingly an object of the present invention to provide a profile inspecting system which will have a small footprint and which can evaluate both images with a single camera with the images being of excellent quality.

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE DRAWINGS

Referring to the drawings:

FIG. 2 is an elevational view of the camera disclosed in FIG. 1;

FIG. 3 is a schematic presentation of the camera's operation;

FIG. 4 shows how a bottle looks in state of the art systems with only one bottle view shown for purposes of clarity; and FIG. 5 shows how a bottle looks in the system disclosed herein with only one bottle shown for purposes of clarity.

DESCRIPTION OF THE PREFERRED EMBODIMENT

Figure 1:
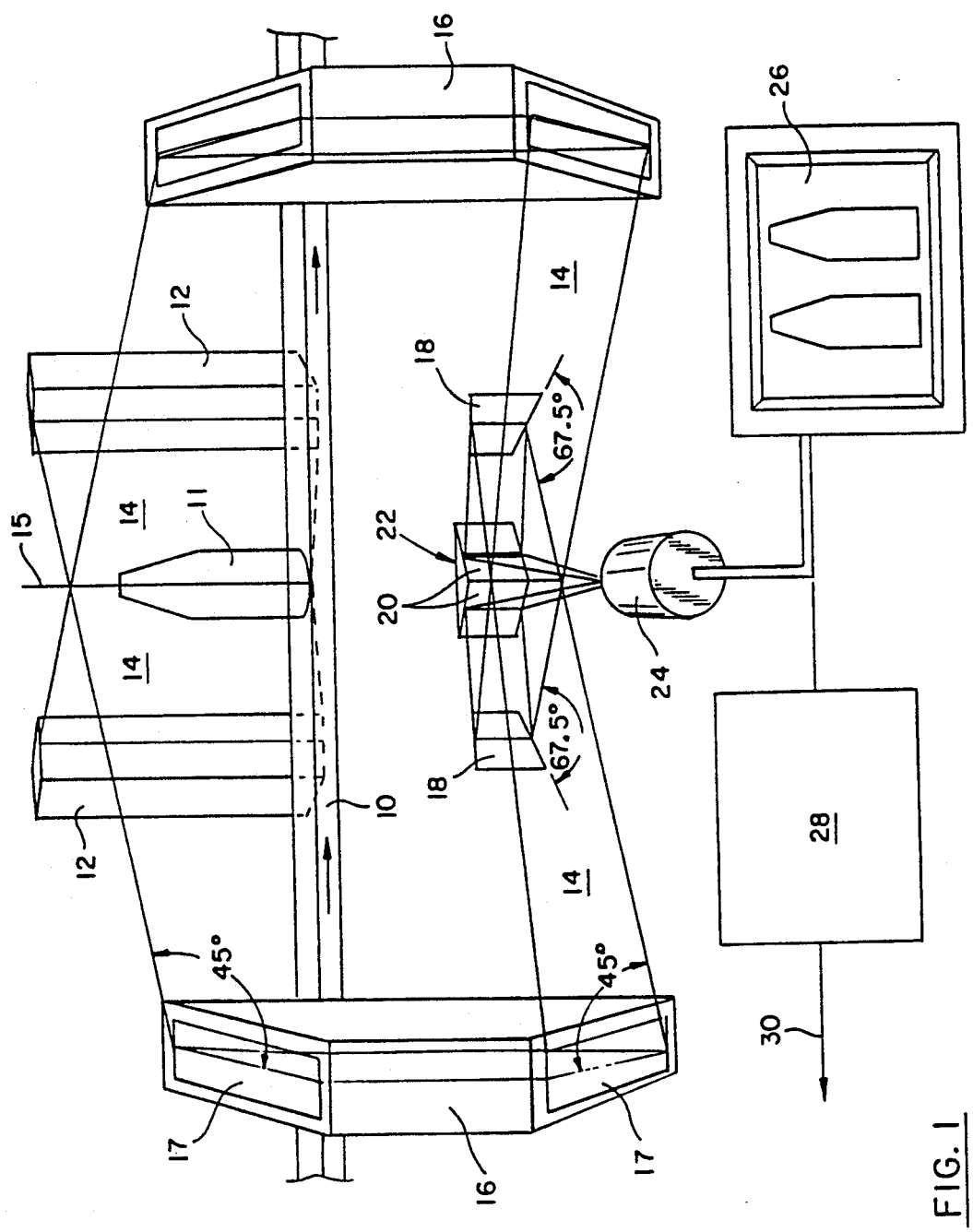
FIG. 1 discloses an oblique schematic view of an inspecting machine made in accordance with the present invention.

A horizontal conveyor 10, moving at a constant speed carries a vertically standing glass container (a bottle) 11 through the illustrated inspection location. At this location a pair of light sources 12 which can be short arc flash tube strobes and which are located behind the conveyor direct diffused back light horizontally, past the bottle at an angle of approximately 45° to the conveyor. As a result, these beams 14 of diffused light intersect perpendicularly through the vertical axis 15 of the bottle when it is located at the inspection location. These beams are larger than the largest container to be inspected so that light will always pass around the entire profile (the sides and top) of a container located at the inspection location. The light from each source is beamed to vertically related mirror pairs 16 which are located in front of the conveyor and which horizontally return the beams to redirecting mirrors 18. The mirrors 17 of these mirror pairs receive these light beams at an angle of approximately 45° (relative to a normal ray). The redirecting mirrors redirect the beams to the reflecting surfaces 20 of a reflecting prism 22 which aim the beams to a corresponding half of the image of a two-dimensional camera 24. Both the redirecting mirrors 18 and the reflecting surfaces 20 of the prism 22 also receive these light beams at an angle of no more than 45° (23.5° and 45° respectively). By configuring the light beam path so that the beam strikes each reflecting surface at no more than about 45° (to a normal ray), unwanted polarization effects will be avoided. And all structures can be located within a very compact footprint. Both images can be presented on a suitable screen 26 and can be evaluated by an image processing computer 28 which can evaluate both views to make sure that the profile is not defective. This image processing computer will issue an acceptance or rejection signal 30. For example, the neck of the container or the entire container may be bent from its desired location. The outer surface of the bottle may have an annular ripple or settle line or the bottle may be a "freak," i.e., a bottle with an unplanned depression. All of these defects can be identified by the image processing computer 28 that will compare the profile of the container with the ideal profile for that container.

As can be seen from FIG. 2, the centerline C.L. of the lens 40 (a lens designed for a 35 mm SLR camera is ideal since it has an image circle much larger than typical electronic sensors and since they have a long back focal distance) is parallel to but vertically below the centerline of the body 42 of the camera which houses the sensor 44 (FIG. 3) by means of an adaptor 46 which secures the camera to the machine frame (not shown). As can be seen from FIG. 3, the lens 40 is selected to have an image circle 48 which is twice the size of the sensor 44 and the adaptor supports the lens so that the center of the lens (the lens axis) is aimed at the base 50 of the bottle and so that the sensor is positioned so that the bottom of the bottle and the conveyor on which it rests is at one edge of the sensor and the top of the bottle (the largest to be inspected) is at the other edge of the sensor. FIG. 4 presents a conventional view of the bottle and FIG. 5 presents a view of a bottle by the disclosed inspection machine. As a result, not only can the profile be evaluated but it is very easy to evaluate the horizontal presentation of the bottom surface of the bottle.

I claim:

1. An inspection machine for inspecting the profile of a vertically standing glass container comprising:
   a conveyor for horizontally displacing a vertically standing glass container through an inspection location, a pair of diffused light sources located behind said conveyor for forwardly directing angularly related beams of light substantially horizontally at a container located at the inspection location, said beams being sufficiently large so that said light beams will pass around the entire profile of a container located at the inspection station, a mirror pair located in front of said conveyor for receiving each of the light beams and redirecting the beams horizontally rearwardly, a reflecting prism having a pair of angularly related reflecting surfaces, one of said prism reflecting surfaces facing one of said mirror pairs and the other one of said prism reflecting surfaces facing the other one of said mirror pairs, a two-dimensional camera having an imaging surface, a pair of redirecting mirrors, one of said redirecting mirrors receiving the beam from said one mirror pair and redirecting the received beam to reflect off said other prism reflecting surface onto one half of said imaging surface, and the other one of said redirecting mirrors receiving the beam from said other mirror pair and redirecting the received beam to reflect off said one prism reflecting surface onto the other half of said imaging surface, and means for evaluating the profile of both container images on said imaging surface.

2. An inspection machine according to claim 1, wherein each of the mirrors in each of said mirror pairs make a 45° angle with the horizontal.

3. An inspection machine according to claim 1, wherein each of said redirecting mirrors, each of said mirrors of said mirror pairs, and each reflecting surface of said reflecting prism receive the light beams at an angle of no more than about 45°.

* * * * *